(12) United States Patent
Sendai et al.

(10) Patent No.: US 6,492,646 B1
(45) Date of Patent: Dec. 10, 2002

(54) METHOD OF AND APPARATUS FOR OBTAINING FLUORESCENCE IMAGE

(75) Inventors: Tomonari Sendai; Kazuo Hakamata; Katsumi Hayashi, all of Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 62 days.

(21) Appl. No.: 09/672,853

(22) Filed: Sep. 29, 2000

(30) Foreign Application Priority Data

Sep. 29, 1999 (JP) .......................................... 11-276381

(51) Int. Cl.[7] .............................................. F21V 9/16
(52) U.S. Cl. .............................. 250/458.1; 250/459.1; 250/361 R; 250/362
(58) Field of Search .......................... 250/458.1, 459.1, 250/361 R, 362

(56) References Cited

U.S. PATENT DOCUMENTS

| | | | |
|---|---|---|---|
| 5,507,287 A | 4/1996 | Palcic et al. ................. | 128/633 |
| 5,657,400 A | * 8/1997 | Granfors et al. ............ | 382/254 |
| 5,749,830 A | 5/1998 | Kaneko et al. | |
| 5,769,792 A | 6/1998 | Palcic et al. ................. | 600/477 |
| 5,802,218 A | 9/1998 | Brailean | |
| 6,002,137 A | 12/1999 | Hayashi ................... | 250/458.1 |
| 6,081,740 A | 6/2000 | Gombrich et al. | |

FOREIGN PATENT DOCUMENTS

| | | | |
|---|---|---|---|
| FR | 2772225 | 6/1999 | |
| JP | 60-54792 | 3/1985 | ............. C02F/3/34 |
| JP | 10-225436 | 8/1998 | ............ A61B/1/04 |
| WO | WO 99/45838 | 9/1999 | |

OTHER PUBLICATIONS

Jahansooz Toofan and Philip R. Watson (Authors); "A New Image Processing Method for Extracting Integrated Intensities from low–energy Electron Diffraction Spots"; pp. 3382–3388; received Apr. 7, 1994; publication Jul. 26, 1994.
George I. Zonios, Robert M. Cothren, Joseph T. Arendt, Jun Wu, Jacques Van Dam, James M. Crawford, Ramasamy Manoharan, and Michael S. Feld (Authors); "Morphological Model of Human Colon Tissue Fluorescence"; pp. 113–122; Feb. 2, 1996.

* cited by examiner

Primary Examiner—Scott J. Sugarman
Assistant Examiner—M. Hasan
(74) Attorney, Agent, or Firm—Sughrue Mion, PLLC

(57) ABSTRACT

Exciting light is projected onto a specimen such as an organic body, and an intensity in at least one wavelength range of fluorescence emitted from the specimen upon excitation by the exciting light is detected. Image data representing a fluorescence image of the specimen is obtained through an operation based on the intensity of the fluorescence. Whether each of pixels forming the fluorescence image is adequate for said operation is determined on the basis of the intensity of the fluorescence of each pixel. The operation is carried out on adequate pixels, which have been determined to be adequate for the operation, to obtain values for the adequate pixels while values which will not visually adversely affect the part of the fluorescence image corresponding to the adequate pixels are allotted to inadequate pixels, which have been determined not to be adequate for said operation.

18 Claims, 5 Drawing Sheets

F I G. 5A
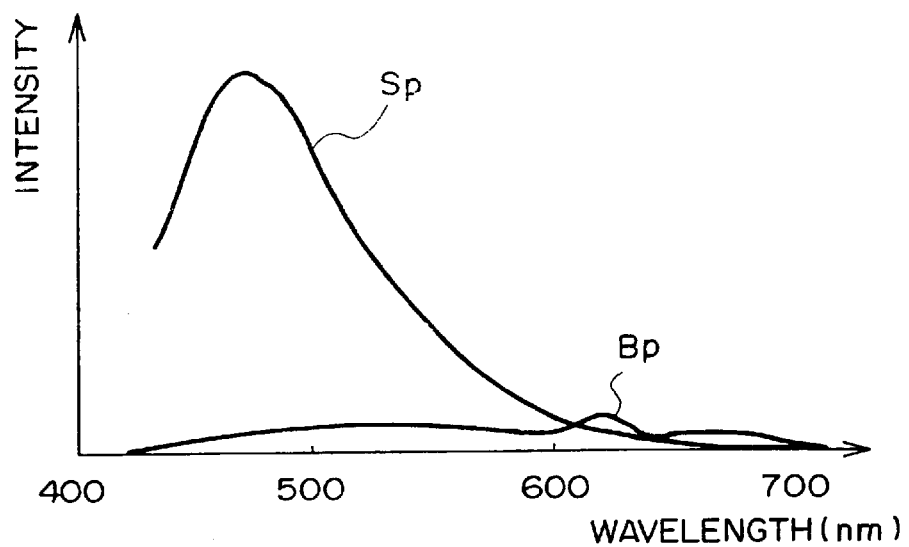
F I G. 5B
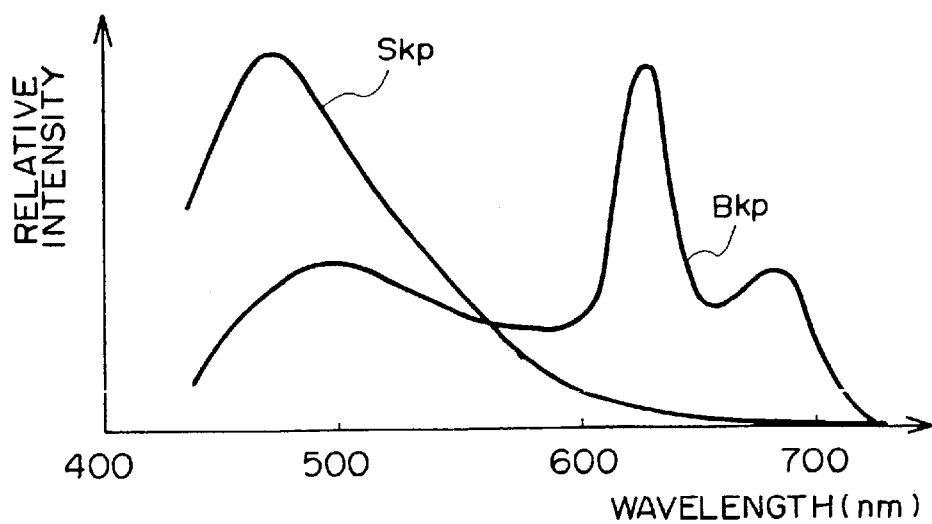

METHOD OF AND APPARATUS FOR OBTAINING FLUORESCENCE IMAGE

BACKGROUND OF THE INVENTION

1. Field of the Invention

This invention relates to a method of and an apparatus for obtaining a fluorescence image on the basis of fluorescence emitted from a specimen such as an organic body upon excitation by exciting light.

2. Description of the Related Art

There has been studied a fluorescence diagnosis system in which exciting light is projected onto an organic body or the like, and information useful for diagnosis is obtained from the intensity or spectral band intensity of fluorescence emitted from the organic body upon excitation by the exciting light. Such a fluorescence diagnosis system includes, for instance, those in which autofluorescence emitted from an organic tissue upon excitation by the exciting light is detected, and those in which fluorescence emitted from an organic tissue which has absorbed a drug for fluorescence diagnosis is detected. Such a fluorescence diagnosis system is generally incorporated in an instrument such as an endoscope, a colposcope, or an operative microscope which is inserted into a body cavity and is used for analyzing conditions of the organic tissue.

At the beginning, an attempt to make a diagnosis on the basis of the intensity of fluorescence emitted from an organic tissue upon excitation by exciting light was made. However, as the relative position between the tissue and the part of the system from which the exciting light is projected onto the tissue such as the distance, angle and the like therebetween changes, the intensity of the exciting light projected onto the organic tissue changes, which results in change in the intensity of the fluorescence emitted from the tissue. Accordingly, the same site of the organic body can emit fluorescence of different intensities depending upon the position of the exciting light projecting part of the fluorescence diagnosis system, which shows that a sufficient diagnostic performance cannot be obtained from the intensity of the fluorescence by itself. Therefore, recently there have been made various attempts to recognize change in the tissue condition on the basis of the fact that the profile of spectral band intensities of the fluorescence changes with change in the tissue condition. For example, a diseased tissue greatly differs from a normal tissue in the ratio of intensity of a green region wavelength component of the fluorescence to intensity of a red region wavelength component of the same. There has been proposed in Japanese Unexamined Patent Publication No. 6(1994)-54792 a fluorescence diagnosis system in which the ratio of intensity of a green region wavelength component to intensity of a red region wavelength component of autofluorescence emitted from an organic tissue to be diagnosed is compared with that of an organic tissue which has been determined to be normal by a different system and whether the organic tissue to be diagnosed is diseased or normal is determined on the basis of the comparison.

Further, we have proposed in Japanese Unexamined Patent Publication No. 10(1998)-225436 a fluorescence diagnosis system in which the intensity in a green wavelength range of fluorescence emitted from an organic tissue is normalized with the intensity of the overall fluorescence (substantially over the entire wavelength range of the spectral bands of the fluorescence) and is compared with that of an organic tissue which has been determined to be normal by a different system, and whether the organic tissue is diseased or normal is determined on the basis of comparison.

However, the intensity of fluorescence of each pixel of an image obtained by taking weak fluorescence emitted from the organic tissue includes noise inherent to the image taking device (e.g., fixed pattern noise, photon shot noise, dark shot noise and read-out noise), noise inherent to the electric processing circuit, noise inherent to the signal transfer system, noise inherent to the optical system (noise due to stray light generated, for instance, by light scattered by dirt or the like adhering to the optical components) and the like, and the intensity of the noise is too large as compared with the intensity of the fluorescence especially for pixels in a region where the intensity of fluorescence is very weak. Accordingly, when the intensity in a green wavelength range of fluorescence emitted from an organic tissue for pixels in a region where the intensity of fluorescence is very weak is normalized by the intensity in a green wavelength range by the intensity of the overall fluorescence, the information obtained by the normalization cannot accurately reflect the condition of the organic tissue since the former intensity and the latter intensity are both very weak and the intensity of the noise components included in the former and latter intensities is too large as compared with the former and latter intensities. When information on such pixels are used as it is in reproduction of an image, the pixels can visually adversely affect observation of the reproduced image.

These problems are common to the fluorescence diagnosis systems in which autofluorescence emitted from an organic tissue upon excitation by the exciting light is detected, and those in which fluorescence emitted from an organic tissue which has absorbed a photosensitive substance for fluorescence diagnosis such as ATX-S10, 5-ALA, Npe6, HAT-D01 or Photofrin-2 (will be referred to as "fluorescence produced by a photosensitive substance" hereinbelow) is detected.

SUMMARY OF THE INVENTION

In view of the foregoing observations and description, the primary object of the present invention is to provide a method of and an apparatus for obtaining a fluorescence image on the basis of fluorescence emitted from a specimen such as an organic body upon excitation by exciting light in which even if adverse pixels, whose intensities include noise in a large proportion, are included in pixels obtained by taking fluorescence emitted from the specimen upon excitation by the exciting light, a fluorescence image which cannot be visually adversely affected by existence of the adverse pixels can be obtained.

In accordance with one aspect of the present invention, there is provided a method of obtaining a fluorescence image comprising the steps of projecting exciting light onto a specimen such as an organic body, detecting an intensity in at least one wavelength range of fluorescence emitted from the specimen upon excitation by the exciting light, and obtaining image data representing a fluorescence image of the specimen through an operation based on the intensity of the fluorescence, wherein the improvement comprises the steps of determining whether each of pixels forming the fluorescence image is adequate for said operation on the basis of the intensity of the fluorescence of each pixel, and carrying out said operation on adequate pixels, which have been determined to be adequate for said operation, to obtain values for the adequate pixels while allotting to inadequate pixels, which have been determined not to be adequate for said operation, values which will not visually adversely affect the part of the fluorescence image corresponding to the adequate pixels.

For example, whether each of pixels is adequate for said operation may be determined by comparing the intensity of fluorescence for the pixel with the value of noise for the pixel which is generated by means for measuring the intensity of fluorescence and has been measured and stored in advance.

When carrying out image processing on the image data, the image processing may be carried out only on the adequate pixels.

The specimen may be an organic body and the fluorescence may be autofluorescence.

The exciting light may be emitted from a GaN semiconductor laser.

In accordance with another aspect of the present invention, there is provided an apparatus for obtaining a fluorescence image comprising an exciting light projecting means for projecting exciting light onto a specimen such as an organic body, a fluorescence intensity measuring means for measuring an intensity in at least one wavelength range of fluorescence emitted from the specimen upon excitation by the exciting light, and an operational processing means for obtaining image data representing a fluorescence image of the specimen through an operation based on the intensity of the fluorescence, wherein the improvement comprises that a determining means determines whether each of pixels forming the fluorescence image is adequate for said operation on the basis of the intensity of the fluorescence of each pixel, and said operational processing means carries out said operation on adequate pixels, which have been determined to be adequate for said operation, to obtain values for the adequate pixels and allots to inadequate pixels, which have been determined not to be adequate for said operation, values which will not visually adversely affect the part of the fluorescence image corresponding to the adequate pixels.

For example, the determining means may determine whether each of pixels is adequate for said operation by comparing the intensity of fluorescence for the pixel with the value of noise for the pixel which is generated by the fluorescence intensity measuring means itself and has been measured and stored in advance.

The apparatus may further comprise an image processing means and the image processing means may carry out the image processing only on the adequate pixels.

The specimen may be an organic body and the fluorescence may be autofluorescence.

The exciting light projecting means may comprise a GaN semiconductor laser as an exciting light source.

The apparatus may be, for instance, an endoscope.

The "noise for the pixel which is generated by the fluorescence intensity measuring means itself" means a part or the whole of noise generated by the fluorescence intensity measuring means between the time the fluorescence intensity measuring means starts to receive the fluorescence and the time it finishes obtaining intensities of the fluorescence in respective wavelength ranges, or noise containing therein a part or the whole of such noise. Typical components of the noise generated by the fluorescence intensity measuring means include noises generated in the circuit of the image taking device, the circuit handling electric signals obtained by the image taking device, the signal transfer circuit for transferring the signals, and the optical system for taking the fluorescence.

When the fluorescence intensity measuring measures an intensity of the fluorescence in only one wavelength range, and the operational processing means obtains image data representing a fluorescence image of the specimen through an operation based on the intensity of the fluorescence in the wavelength range, the operation includes, for instance, an operation for allotting to pixels values reflecting the intensity of the fluorescence and an operation carried out between the intensity of the fluorescence in the wavelength range and a reference intensity obtained from light reflected by the specimen when a near infrared ray is projected onto the specimen. When the fluorescence intensity measuring measures intensities of the fluorescence in two or more wavelength ranges, and the operational processing means obtains image data representing a fluorescence image of the specimen through an operation based on the intensities of the fluorescence in the wavelength ranges, the operation includes, for instance, an operation carried out between the intensities of the fluorescence and an operation carried out among the intensities of the fluorescence in the wavelength ranges and a reference intensity obtained from light reflected by the specimen when a near infrared ray is projected onto the specimen.

When the amount of fluorescence received by a pixel is very small and accordingly the amount of noise included in the value for the pixel is too large relative to the amount of the fluorescence for the operation to provide a value which correctly reflects the condition of the specimen, the pixel is determined to be an inadequate pixel.

On the other hand, when the amount of fluorescence received by a pixel is large and accordingly the amount of noise included in the value for the pixel is relatively small so that the operation can provide a value which correctly reflects the condition of the specimen, the pixel is determined to be an adequate pixel.

The adequate and inadequate pixels do not exist from the beginning but are set on the basis of the amount of noise generated by the fluorescence intensity measuring means by itself and the measured amount of fluorescence.

Auto fluorescence emitted from the inside of an organic body is sometimes called "in vivo autofluorescence".

In accordance with the present invention, since values which will not visually adversely affect the part of the fluorescence image corresponding to the adequate pixels are allotted to inadequate pixels, a fluorescence image which is free from adverse influence of inadequate pixels and is excellent in quality can be obtained.

Further, since the operation is carried out only on adequate pixels, the operation time can be shortened.

When whether each of pixels is adequate for said operation may be determined by comparing the intensity of fluorescence for the pixel with the value of noise for the pixel which is generated by means for measuring the intensity of fluorescence and has been measured and stored in advance, adequate pixels can be more rationally distinguished from inadequate pixels.

When image processing is carried out only on the adequate pixels, a fluorescence image which is free from adverse influence of inadequate pixels can be reproduced and the processing time can be shortened.

Use of a GaN semiconductor laser as the exciting light source contributes to miniaturization of the apparatus and reduction of the cost.

The method and apparatus of the present invention can be used to observe the condition of the inside of an organic body through autofluorescence emitted from the organic body upon excitation by the exciting light. That is, the present invention can be applied to an endoscope.

BRIEF DESCRIPTION OF THE DRAWINGS

FIG. 5A is a view showing distributions of spectral intensity of fluorescence emitted from a normal tissue and a diseased tissue, FIG. 5B is a view showing profiles of normalized intensity of fluorescence emitted from a normal tissue and a diseased tissue.

DESCRIPTION OF THE PREFERRED EMBODIMENT

Figure 1:
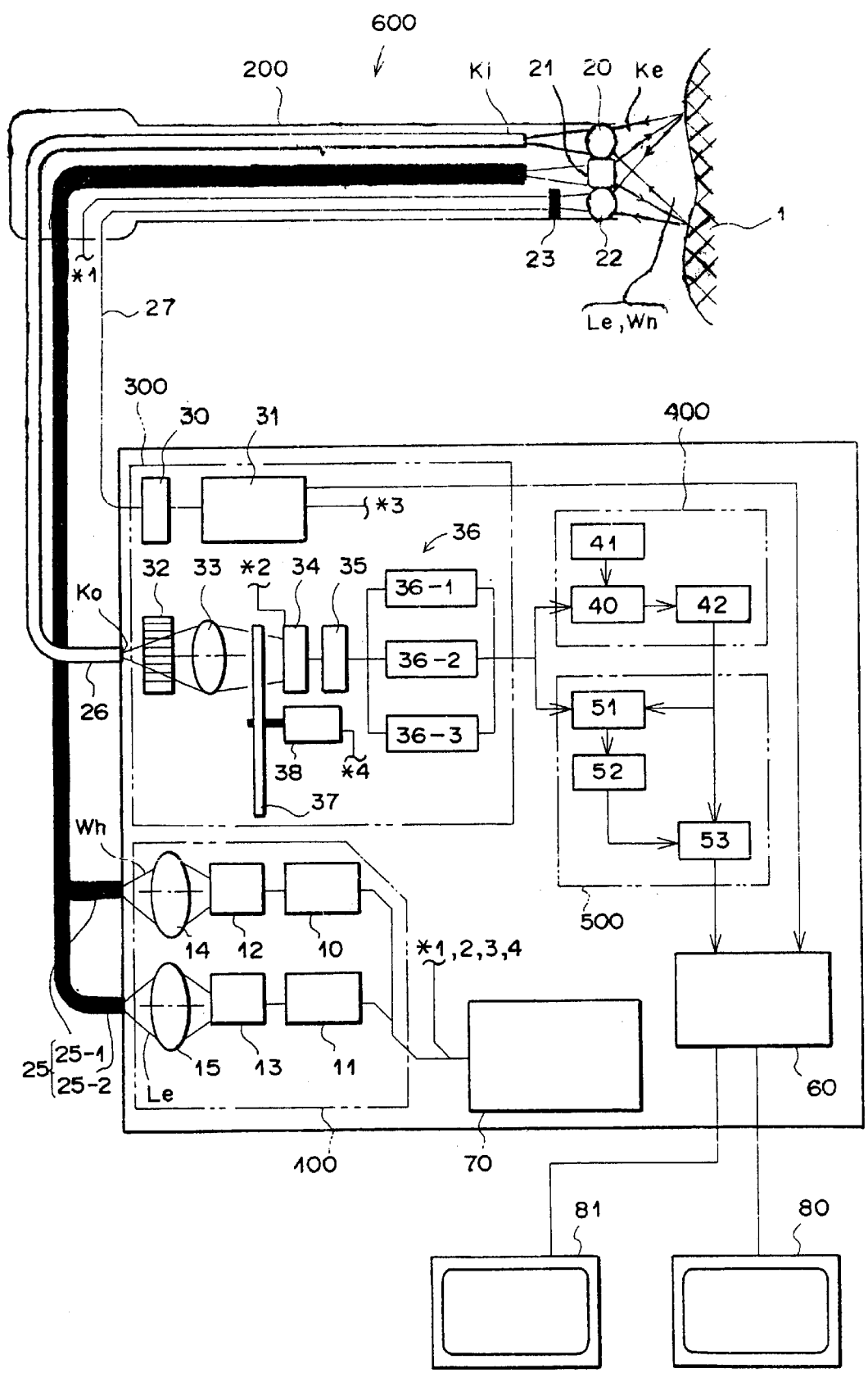
FIG. 1 is a schematic view showing a fluorescence endoscope in accordance with an embodiment of the present invention.

FIG. 1 shows a fluorescence endoscope in accordance with an embodiment of the present invention.

As shown in FIG. 1, the fluorescence endoscope 600 comprises a light source unit 100 having a white light source 12 and an exciting light source 13, and a flexible insertion unit 200 which leads white light Wh and exciting light Le to an organic tissue 1 and takes a normal image of the organic tissue 1 formed by the white light Wh while propagating through an optical fiber 26 an autofluorescence image formed by autofluorescence emitted from the organic tissue 1 upon excitation by the exciting light Le. The normal image taken by the insertion unit 200 is taken in by an image take-in unit 300. The image take-in unit 300 takes in the normal image and stores the image data as normal image data. Further, the image take-in unit 300 receives the fluorescence image divided into three wavelength ranges and stores the three images corresponding to the three wavelength ranges in the form of intensities of fluorescence in the three wavelength ranges (intensities of fluorescence in the three wavelength ranges for each pixel forming the fluorescence image). The intensities of fluorescence stored in the image take-in unit 300 are input into a determination unit 400 and the determination unit 400 determines whether each of pixels forming the fluorescence image is adequate for a predetermined operation and stores the positions of pixels which are determined to be inadequate (the positions will be referred to as "the inadequate pixel positions", hereinbelow) as inadequate pixel position data. A distinguishing operation unit 500 carries out a distinguishing operation for distinguishing a normal tissue from a diseased tissue on the basis of the intensities of fluorescence in the three wavelength ranges while referring to the inadequate pixel position data, and stores the result of the operation as image data for distinguishment.

The normal image data output from the image take-in unit 300 and the image data for distinguishment output from the distinguishing operation unit 500 are input into a video signal processing circuit 60 and are converted to video signals. The video signals are respectively input into a normal image TV monitor 80 and a fluorescence image TV monitor 81 provided outside the endoscope 600 and a normal image and a fluorescence image are reproduced on the respective monitors 80 and 81 on the basis of the video signals. A control unit 70 controls the overall endoscope 600.

The white light source 12 of the light source unit 100 is connected to a power source 10 which is controlled by the control unit 70. The white light source 12 is energized to emit white light pulses Wh in a cycle of a 1/60 second and the white light pulses Wh are condensed by a white light condenser lens 14 and introduced into a white light guide 25-1 which is formed of multi-component glass optical fiber and connected to the light source unit 100.

The exciting light source 13 comprises a semiconductor laser and driven by an LD power source 11, which is controlled by the control unit 70, to generate exciting light pulses Le at about 410 nm in a cycle of a 1/60 second at timings which do not overlap with the timing at which the white light pulses Wh are emitted. The exciting light pulses Le are condensed by an exciting light condenser lens 15 and introduced into an exciting light guide 25-2 which is formed of silica optical fiber and connected to the light source unit 100.

The white light guide 25-1 and the exciting light guide 25-2 are bundled into a cable.

The cable of the white light guide 25-1 and the exciting light guide 25-2 extends through the insertion unit 200 and is provided with an illumination lens 5 at the front end thereof. The white light pulses Wh and the exciting light pulses Le respectively emitted from the white light guide 25-1 and the exciting light guide 25-2 are projected onto the organic tissue 1 through the illumination lens 5. A normal image of the organic tissue 1 illuminated by the white light pulses Wh is formed on a light receiving surface of a normal image taking CCD device 23 by a normal image objective lens 22 and converted to an electric image signal by the CCD device 22. The image signal representing the normal image of the organic tissue 1 is transferred to the image take-in section 300 through a CCD cable 27. An image formed by fluorescence Ke emitted from the organic tissue 1 upon excitation by the exciting light pulses Le is formed on an end face Ki of a fluorescence image optical fiber 26 by a fluorescence image objective lens 20 and the fluorescence image propagates through the fluorescence image optical fiber 26 to the other end face Ko of the fluorescence image optical fiber 26 connected to the image take-in unit 300.

The image take-in unit 300 is provided with a normal A/D converter 30 which digitizes the electric image signal representing the normal image of the organic tissue 1 transferred through the CCD cable 27 and a normal image memory 31 which stores the digitized image signal. The image take-in unit 300 is further provided with an optical system which takes in the fluorescence image, propagating to the end face Ko of the fluorescence image optical fiber 26, through an exciting light cut filter 32 which cuts light of a wavelength not longer than about 410 nm, and forms a fluorescence image on a light receiving face of a high-sensitive image taking device 34 through a fluorescence condenser lens 33; an A/D converter 35 which digitizes an electric image signal obtained by converting the fluorescence image by the high-sensitive image taking device 34; and a fluorescence image memory means 36 which stores the digitized image signals representing the fluorescence images in the respective wavelength ranges. Each of the digitized image signals representing the fluorescence images in the respective wavelength ranges are made up of a number of image signal components each representing an intensity of fluorescence for each pixel, and the digitized image signals are stored respectively in memories 36-1, 36-2 and 36-3 of the fluorescence image memory means 36 as will become apparent later.

Figure 2:
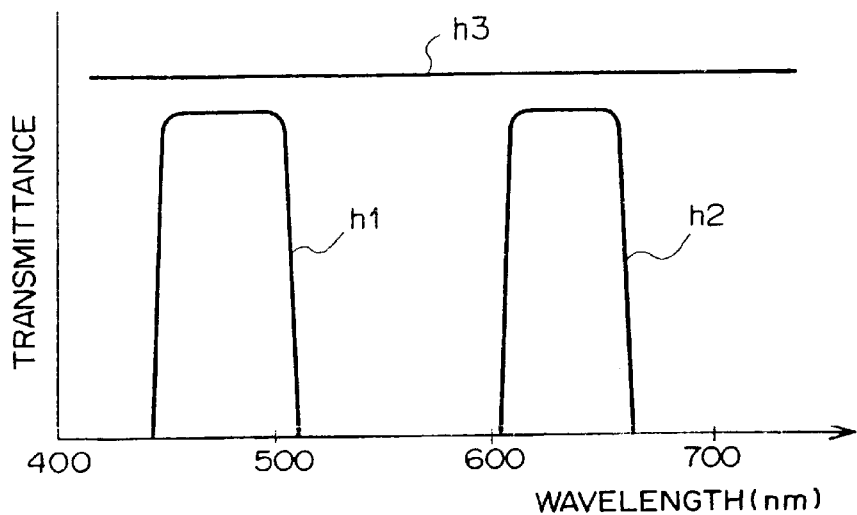
FIG. 2 is a view showing transmission characteristics of the filters forming the color separation filter.
Figure 3:
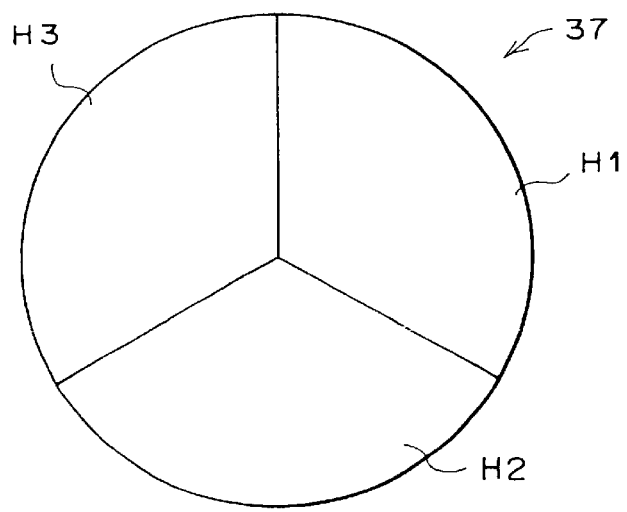
FIG. 3 is a view showing the color separation filter.

A color separation filter 37 is inserted between the high-sensitive image taking device 34 and the fluorescence condenser lens 33. As shown in FIG. 3, the color separation filter 37 comprises three filter segments H1, H2 and H3 which respectively transmit fluorescence in wavelength ranges h1, h2 and h3. As shown in FIG. 2, the wavelength range h1 is a wavelength range near 480 nm, the wavelength range h2 is a wavelength range near 630 nm and the wavelength range h3 is a whole wavelength range. The color separation filter 37 is rotated by an electric motor 38 in synchronization with the image taking cycle (1/60 seconds) of the high-sensitive image taking device 34. By virtue of the color separation filter 37, the fluorescence image is divided into the three wavelength ranges h1 to h3, and the intensities of the fluorescence in the wavelength range h1 for the corresponding pixels are digitized and values representing the digitized intensities of the fluorescence are stored in the first memory 36-1 of the fluorescence image memory means 36, the intensities of the fluorescence in the wavelength range h2 for the corresponding pixels are digitized and values representing the digitized intensities of the fluorescence are stored in the second memory 36-2, and the intensities of the fluorescence in the wavelength range h3 for the corresponding pixels are digitized and values representing the digitized intensities of the fluorescence are stored in the third memory 36-3.

The determination unit 400 is provided with a determination operation section 40 which compares the values representing the digitized intensities of the fluorescence (will be referred to simply as "intensities of the fluorescence", hereinbelow) in the three wavelength ranges with noise image data which has been stored in a noise level memory 41, thereby dividing the pixels of the fluorescence image into adequate pixels and inadequate pixels. Positions of the inadequate pixels are stored in an inadequate pixel position data memory 42 as inadequate pixel position data.

The distinguishing operation unit 500 comprises a distinguishing operation section 51 which carries out a distinguishing operation for distinguishing a normal tissue from a diseased tissue on the basis of the intensities of fluorescence in the three wavelength ranges stored in the fluorescence image memory means 36 while referring to the inadequate pixel position data. The result of the operation of the distinguishing operation section 51 is stored in a distinguishing image memory 52 as image data for distinguishment.

Operation of the fluorescence endoscope 600b of this embodiment will be described, hereinbelow.

A white light pulse Wh emitted from the white light source 12 is led to the white light guide 25-1, propagates through the white light guide 25-1 and illuminates the organic tissue 1 through the illumination lens 21. An image of the organic tissue 1 illuminated by the white light pulse Wh is formed on the light receiving face of the normal image taking CCD device 23 by the normal image objective lens 22. The normal image taking CCD device 23 converts the normal image to a normal image signal representing the normal image, and the normal image signal is digitized by the A/D converter 30 and stored in the normal image memory 31.

After the end of projection of the white light pulse Wh, an exciting light pulse Le is emitted from the exciting light source 13 and is projected onto the organic tissue 1 through the exciting light condenser lens 15, the exciting light guide 25-2 and the illumination lens 21.

Auto fluorescence Ke emitted from the organic tissue 1 upon excitation by the exciting light pulse Le is caused to form an image on the end face Ki of the fluorescence image optical fiber 26 by the fluorescence image objective lens 20 and the fluorescence image is propagated through the fluorescence image optical fiber 26 to the other end face Ko. The fluorescence image is then focused on the light receiving face of the high-sensitive image taking device 34 through the exciting light cut filter 32 and the filter segment H1 of the color separation filter 37 with the exciting light contained in the fluorescence image removed by the cut filter 32. Then an electric image signal representing the fluorescence image is read out from the image taking device 34 and is digitized by the A/D converter 35 (to intensities of the fluorescence for the respective pixels). The digital image signal thus obtained is stored in the first memory 36-1 of the fluorescence image memory means 36.

Thereafter another exciting light pulse Le is emitted from the exciting light source 13 and a fluorescence image is taken through the filter segment H2 of the color separation filter 37 and intensities of the fluorescence for the respective pixels thus obtained are stored in the second memory 36-2 of the fluorescence image memory means 36. Thereafter still another exciting light pulse Le is emitted from the exciting light source 13 and a fluorescence image is taken through the filter segment H3 of the color separation filter 37 and intensities of the fluorescence for the respective pixels thus obtained are stored in the third memory 36-3 of the fluorescence image memory means 36. In this manner, fluorescence images in the three wavelength ranges h1, h2 and h3 are taken as one set and the intensities of fluorescence for each pixel of the fluorescence images in the three wavelength ranges h1, h2 and h3 are stored respectively in the first to third memories 36-1 to 36-3 as intensities of fluorescence Dh1, Dh2 and Dh3.

Then the intensities of fluorescence Dh1, Dh2 and Dh3 are input into the determination operation section 40 which compares the digitized intensities of the fluorescence Dh1, Dh2 and Dh3 in the three wavelength ranges with noise image data which has been stored in the noise level memory 41, thereby dividing the pixels of the fluorescence image into adequate pixels and inadequate pixels. Positions of the inadequate pixels are stored in the inadequate pixel position data memory 42 as inadequate pixel position data.

Figure 4:
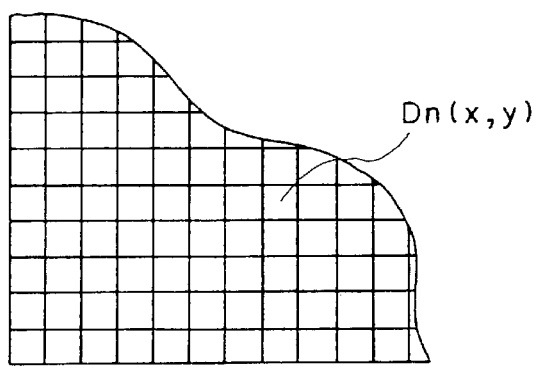
FIG. 4 is a view showing positions (x, y) of pixels for the noise image data.

A specific example of the method of distinguishing inadequate pixels from adequate pixels will be described in detail, hereinbelow. As shown in FIG. 4, the noise image data Dn stored in the noise level memory 41 comprises matrix-like values obtained in advance for the positions (x, y) of the respective matrix-like pixels by measurement or the like. The values Dn(x, y) of the noise image data Dn can be obtained, for instance, by storing the values for respective pixels which are obtained by digitizing the image signal output from the high-sensitive image taking device 34 in a dark place where no light reaches without use of the white light pulse Wh or the exciting light pulse Le and may be considered to values of noises generated by the image taking device 34, the electric processing circuit, and the signal transfer system.

When the intensities of fluorescence in the three wavelength ranges h1, h2 and h3 for a pixel in a position (X1, Y1), i.e., Dh1(X1, Y1), Dh2(X1, Y1), Dh3(X1, Y1), are all smaller than a predetermined coefficient (α) times the value Dn(X1, Y1) for the same pixel, the pixel is determined to be an inadequate pixel. That is, a pixel (X1, Y1) is an inadequate pixel when $$Dh1(X1, Y1) < \alpha \times Dn(X1, Y1) \quad (1)$$

and $$Dh2(X1, Y1) < \alpha \times Dn(X1, Y1) \quad (2)$$

and $$Dh3(X1, Y1) < \alpha \times Dn(X1, Y1) \quad (3)$$

When at least one of the conditions (1) to (3) is not satisfied, the pixel is determined to be an adequate pixel. In this manner, whether the pixel is adequate or inadequate is determined for all the pixels and positions of the inadequate pixels are stored in an inadequate pixel position data memory 42 as inadequate pixel position data GF.

Then the distinguishing operation section 51 carries out an operation among the intensities of the fluorescence Dh1, Dh2 and Dh3 in the three wavelength ranges. Specifically, an image data for distinguishment Sh is obtained by dividing a fluorescence intensity difference component between the intensity Dh1 in the wavelength range h1 (near 480 nm) and the intensity Dh2 in the wavelength range h2 (near 630 nm) by the intensity Dh3 in the wavelength range h3 (the whole wavelength range). That is, $$Sh(x, y) = \{Dh2(x, y) - Dh1(x, y)\} / Dh3(x, y)$$
$$= Dh2(x, y) / Dh3(x, y) - Dh1(x, y) / Dh3(x, y)$$

When a spectral intensity distribution Sp of autofluorescence emitted from a normal organic tissue is compared with that Bp of autofluorescence emitted from a diseased organic tissue, the autofluorescence emitted from a normal organic tissue is higher in intensity than the autofluorescence emitted from a diseased organic tissue as shown in FIG. 5A. However, when a profile Skp of normalized intensity (normalized by the integrated intensity of fluorescence in the whole wavelength range) of fluorescence emitted from a normal organic tissue, that is, a profile obtained on the basis of the ratio of the integral value of the intensity of fluorescence in a particular wavelength range to the integral value of the intensity of fluorescence in the whole wavelength range, is compared with that Bkp of normalized intensity of fluorescence emitted from a diseased organic tissue (the former is compared with the latter after they are converted so that the integral values of the intensity of fluorescence in the whole wavelength range for the former and the latter become equal to each other, e.g., to 1), the normalized intensity of fluorescence emitted from the normal organic tissue is higher than that of fluorescence emitted from the diseased organic tissue in a wavelength range not longer than 550 nm (especially near 480 nm) and is lower than that of fluorescence emitted from the diseased organic tissue in a wavelength range not shorter than 600 nm (especially near 630 nm) as shown in FIG. 5B.

Figure 6A:
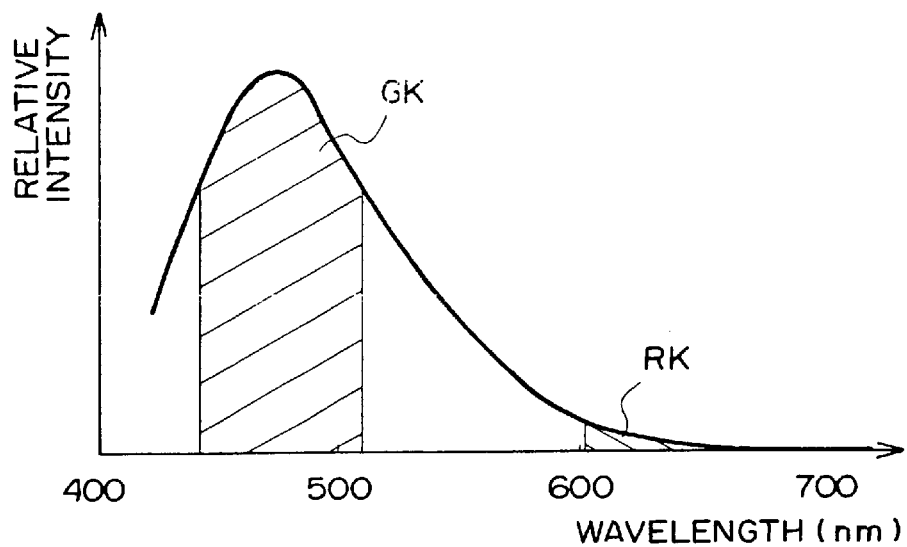
FIG. 6A is a view showing the normalized intensity of fluorescence emitted from a normal tissue near 480 nm and 630 nm.
Figure 6B:
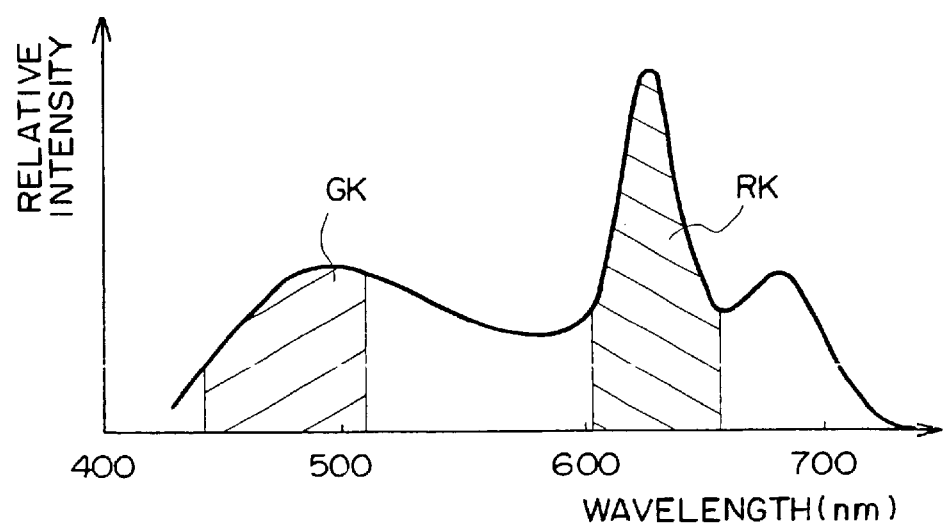
FIG. 6B is a view showing the normalized intensity of fluorescence emitted from a diseased tissue near 480 nm and 630 nm.

Accordingly, when the image data for distinguishment Sh(x, y) obtained by subtracting the normalized intensity Rk (Dh1(x, y)/Dh3(x, y)) in the wavelength range near 630 nm from the normalized intensity Gk (Dh2(x, y)/Dh3(x, y)) in the wavelength range near 480 nm is large, the organic tissue is determined to be normal (FIG. 6A), and when the image data for distinguishment Sh(x, y) is small, the organic tissue is determined to be diseased (FIG. 6B).

The operation is carried out referring to the inadequate pixel position data GF and is not carried out on the inadequate pixels. On the other hand, the operation is carried out on the adequate pixels, and the image data for distinguishment Sh(x, y) for each adequate pixel is stored in the distinguishing image memory 52. Thus, pixels in a region where the amount of fluorescence received by the high-sensitive image taking device 34 is very small and the amount of noise included in the values for the pixels is too large relative to the amount of the fluorescence for the operation to provide values which correctly reflect the condition of the specimen are determined to be inadequate pixels and the operation is not carried out on the pixels.

Figure 7:
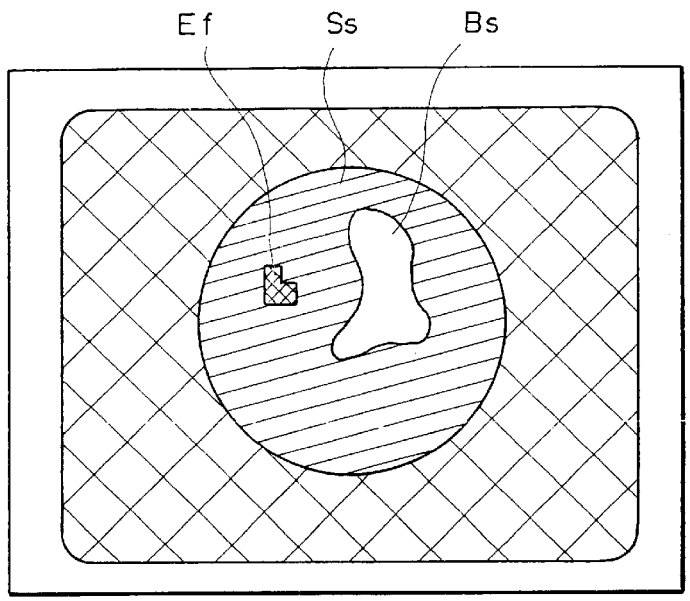
FIG. 7 is a view showing an example of fluorescence image displayed on a CRT.

The distinguishing operation section 51 does not carry out the operation for distinguishing a normal tissue from a diseased tissue on the inadequate pixels and instead allots to each of the inadequate pixels, for instance, a value which causes the inadequate pixel to be displayed as a dark point on the fluorescence image TV monitor 81. As a result, on the fluorescence image TV monitor 81, a diseased tissue Bs is displayed light, a normal tissue is displayed dark and the part Ef corresponding to the inadequate pixels is displayed dark not to visually adversely affect the image displayed on the fluorescence image TV monitor 81 as shown in FIG. 7. Otherwise, 0, the same value as the values for the pixels corresponding to the normal tissue or a value which causes the inadequate pixel to be displayed in the same color and the same brightness as the background of the image on the fluorescence image TV monitor 81 may be allotted to each of the inadequate pixels.

The image data for distinguishment Sh(x, y) stored in the distinguishing image memory 52 is input into the video signal processing circuit 60 after subjected to image processing by the image processing section 53 (e.g., edge enhancing processing, smoothing processing, filtering processing, histogram correction processing and the like) and converted to a video signal. The video signal is input into the fluorescence image TV monitor 81 and a fluorescence image is reproduced on the basis of the video signal. The inadequate pixel position data GF is input into the image processing section 53 from the inadequate pixel position data memory 42 and the image processing section 53 does not carry out the image processing on the inadequate pixels. That is, the values allotted to the inadequate pixels by the distinguishing operation section 51 are input into the video signal processing circuit 60 as they are.

The normal image signal stored in the normal image memory 31 is converted to a video signal by the video signal processing circuit 60 and a normal image is reproduced on the normal image TV monitor 80 on the basis of the video signal.

The image data for distinguishment Sh may be obtained through various operations other than the operation in which a fluorescence intensity difference is divided by the intensity in the whole wavelength range. For example, the image data for distinguishment Sh may be obtained by dividing the intensity of a fluorescence component near 480 nm by the intensity of a fluorescence component near 630 nm.

Further, though in the embodiment described above, the present invention is applied to a system for taking an autofluorescence image, the present invention may be applied also to a system for taking an image formed by fluorescence produced by a photosensitive substance.

Further, though in the embodiment described above, the present invention is applied to a fluorescence endoscope, the present invention may be applied also a colposcope, an operative microscope and the like.

Though, in the embodiment described above, the fluorescence image is divided into three wavelength ranges, a wavelength range near 480 nm, a wavelength range near 630 nm and a whole wavelength range, the fluorescence image may be divided into other wavelength ranges and into other number of wavelength ranges.

Since the value of noise contained in the value for each pixel of a fluorescence image differs according to the conditions such as the temperature and the like, different pieces of noise image data Dn(x, y) may be stored in the noise level memory 41 so that one of the pieces of noise image data is selected according to the condition of measurement.

Instead of measuring the noise image data for each pixel, an average of the values of noise may be used for all the pixels. Further, the noise image data may include noises due to dust adhering to the optical system for inputting the fluorescence into the fluorescence image taking device.

Further, though, in the embodiment described above, when the intensities of fluorescence in the three wavelength ranges h1, h2 and h3 for a pixel in a position (X1, Y1), i.e., Dh1(X1, Y1), Dh2(X1, Y1) and Dh3(X1, Y1), are all smaller than a predetermined coefficient ($\alpha$) times the value Dn(X1, Y1) of noise image data for the same pixel, the pixel is determined to be an inadequate pixel, the pixel may be determined to be an inadequate pixel when one or two of Dh1(X1, Y1), Dh2(X1, Y1) and Dh3(X1, Y1) is smaller than the predetermined coefficient ($\alpha$) times the value Dn(X1, Y1) of noise image data for the same pixel.

The coefficient $\alpha$ may be a fixed value or may be selected by the operator, e.g., by operating a dial, a foot switch or the like.

In the case where it is expected that the amount of fluorescence emitted from an organic tissue is small and the value of each pixel becomes small, the amount of fluorescence received by the high-sensitive image taking device for the fluorescence image may be read out in advance, for instance, by binning-and a plurality of pixels (e.g., 2×2 pixels or 4×4 pixels) may be handled as a single pixel. That is, when the processing described above is carried out in this state, the amount of fluorescence can be apparently increased and a part of pixels which will be otherwise determined to be inadequate can be handled as an adequate pixel.

The structure of the system for processing image data need not be limited to that shown in FIG. 1 but, for instance, the structure of the determination unit 400 and/or the distinguishing operation unit 500 may be changed.

Further, both the fluorescence image and the normal image may be displayed on a single TV monitor.

Further, the wavelength of the exciting light Le need not be limited to a wavelength near 410 nm but may be of any wavelength so long as it can efficiently cause the organic tissue to emit fluorescence.

Figure 8A:
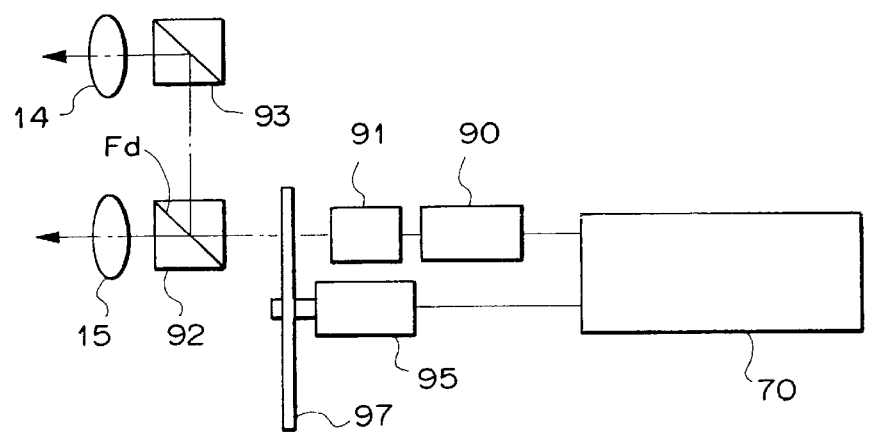
FIG. 8A is a view showing a modification of the endoscope shown in FIG. 1.
Figure 8B:
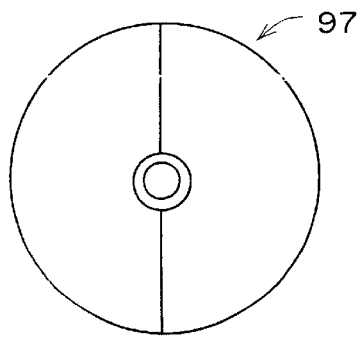
FIG. 8B is a view showing a filter employed in the modification shown in FIG. 8A.

FIGS. 8A and 8B show a modification of the endoscope shown in FIG. 1. In this modification, the white light Wh and the exciting light Le are emitted from a single light source 91 energized by a single power source 90. That is, the light source 91 emits light in a wavelength range including the wavelength range of the white light Wh and the wavelength range of the exciting light and the light emitted from the light source 91 is passed through a split filter 97, which comprises a pair of semicircular filter segments as shown in FIG. 8B, one of which transmits light in the wavelength range of the exciting light Le and the other of which transmits light in the wavelength range of white light Wh. The split filter 97 is rotated so that the segments are alternately inserted into the optical path of light emitted from the light source 91, whereby the white light Wh and the exciting light Le alternately emanate from the split filter 97. The exciting light Le emanating from the, split filter 97 passes through a cube beam splitter 92, having a dichroic face Fd which reflects the white light Wh and transmits the exciting light Le, and enters the exciting light guide 25-2 (FIG. 1) through the condenser lens 15. The white light Wh emanating from the split filter 97 is reflected by the cube beam splitter 92 to impinge upon another cube beam splitter 93 and is reflected by the cube beam splitter 93 to enter the white light guide 25-1 (FIG. 1) through the condenser lens 14.

Though, in the embodiment described above, the CCD image taking device 23 for taking a normal image is disposed on the front end of the endoscope, it may be disposed in the image take-in unit 300 by the use of an image fiber. Further, an image fiber and an image taking device may be used in common for taking a fluorescence image and a normal image. In this case, an optical filter or the like for separating the fluorescence image and the normal image from each other should be provided in front of the image taking device.

Further, the high-sensitive image taking device 34 for a fluorescence image may be provided in the insertion unit 200. It is further possible to use a single image taking device disposed in the insertion unit 200 in common for taking a fluorescence image and a normal image. In this case, a mosaic filter or the like which is equivalent to the color separation filter 37 should be provided in front of the single image taking device.

When a GaN semiconductor laser is used as the exciting light source, the apparatus can be small in size and low in cost.

As can be understood from the description above, in accordance with the present invention, even if adverse pixels, whose intensities include noise in a large proportion, are included in pixels obtained by taking fluorescence emitted from the specimen upon excitation by the exciting light, a fluorescence image which cannot be visually adversely affected by existence of the adverse pixels can be obtained. Further, by not carrying out the operation on the adverse pixels, the image data processing time can be shortened.

In addition, all of the contents of Japanese Patent Application Nos. 11(1999)-276381 and 2000-231894 are incorporated into this specification by reference.

What is claimed is:

1. A method of obtaining a fluorescence image comprising the steps of projecting exciting light onto a specimen such as an organic body, detecting an intensity in at least one wavelength range of fluorescence emitted from the specimen upon excitation by the exciting light, and obtaining image data representing a fluorescence image of the specimen through an operation based on the intensity of the fluorescence, wherein the improvement comprises the steps of determining whether each of pixels forming the fluorescence image is adequate for said operation on the basis of the intensity of the fluorescence of each pixel, and carrying out said operation on adequate pixels, which have been determined to be adequate for said operation, to obtain values for the adequate pixels while allotting to inadequate pixels, which have been determined not to be adequate for said operation, values which will not visually adversely affect the part of the fluorescence image corresponding to the adequate pixels.

2. A method as defined in claim 1 further comprising the step of carrying out image processing on the image data, wherein the image processing is carried out only on the adequate pixels.

3. A method as defined in claim 1 in which the specimen is an organic body and the fluorescence is in vivo autofluorescence.

4. A method of obtaining a fluorescence image comprising the steps of:

projecting exciting light onto a specimen such as an organic body;

detecting an intensity in at least one wavelength range of fluorescence emitted from the specimen upon excitation by the exciting light;

obtaining image data representing a fluorescence image of the specimen through an operation based on the intensity of the fluorescence; and determining whether each of pixels forming the fluorescence image is adequate for said operation on the basis of the intensity of the fluorescence of each pixel and carrying out said operation on adequate pixels, which haven been determined to be adequate for said operation, to obtain values for the adequate pixels while allotting to inadequate pixels, which have been determined not to be adequate for said operation, values which will not visually adversely affect the part of the fluorescence image corresponding to the adequate pixels;

wherein the adequacy of each pixel is determined by comparing the intensity of fluorescence for the pixel with the value of noise for the pixel which is generated by means for measuring the intensity of fluorescence and has been measured and stored in advance.

5. A method of obtaining a fluorescence image comprising the steps of:

projecting exciting light onto a specimen such as an organic body;

detecting an intensity in at least one wavelength range of fluorescence emitted from the specimen upon excitation by the exciting light;

obtaining image data representing a fluorescence image of the specimen through an operation based on the intensity of the fluorescence; and determining whether each pixel forming the fluorescence image is adequate for said operation on the basis of the intensity of the fluorescence of each pixel and carrying out said operation on adequate pixels, which haven been determined to be adequate for said operation, to obtain values for the adequate pixels while allotting to inadequate pixels, which have been determined not to be adequate for said operation, values which will not visually adversely affect the part of the fluorescence image corresponding to the adequate pixels;

wherein said exciting light is emitted from a GaN semiconductor laser.

6. An apparatus for obtaining a fluorescence image comprising an exciting light projecting means for projecting exciting light onto a specimen such as an organic body, a fluorescence intensity measuring means for measuring an intensity in at least one wavelength range of fluorescence emitted from the specimen upon excitation by the exciting light, and an operational processing means for obtaining image data representing a fluorescence image of the specimen through an operation based on the intensity of the fluorescence, wherein the improvement comprises that a determining means determines whether each of pixels forming the fluorescence image is adequate for said operation on the basis of the intensity of the fluorescence of each pixel, and said operational processing means carries out said operation on adequate pixels, which have been determined to be adequate for said operation, to obtain values for the adequate pixels and allots to inadequate pixels, which have been determined not to be adequate for said operation, values which will not visually adversely affect the part of the fluorescence image corresponding to the adequate pixels.

7. An apparatus as defined in claim 6 further comprising an image processing means, wherein the image processing means carries out the image processing only on the adequate pixels.

8. An apparatus as defined in claim 6 in which the specimen is an organic body and the fluorescence is in vivo autofluorescence.

9. An apparatus as defined in claim 6 in which the apparatus is an endoscope.

10. An apparatus for obtaining a fluorescence image comprising:

an exciting light projecting means for projecting exciting light onto a specimen such as an organic body;

a fluorescence intensity measuring means for measuring an intensity in at least one wavelength range of fluorescence emitted from the specimen upon excitation by the exciting light;

an operational processing means for obtaining image data representing a fluorescence image of the specimen through an operation based on the intensity of the fluorescence;

a determining means for determining whether each of pixels forming the fluorescence image is adequate for said operation on the basis of the intensity of the fluorescence of each pixel; and said operational processing means carrying out said operation on adequate pixels to obtain values for the adequate pixels, which haven been determined to be adequate for said operation, while allotting to inadequate pixels, which have been determined not to be adequate for said operation, values which will not visually adversely affect the part of the fluorescence image corresponding to the adequate pixels;

said determining means determining whether each of pixels is adequate for said operation by comparing the intensity of fluorescence for the pixel with the value of noise for the pixel which is generated by the fluorescence intensity measuring means itself and has been measured and stored in advance.

11. An apparatus for obtaining a fluorescence image comprising:

an exciting light projecting means for projecting exciting light onto a specimen such as an organic body;

a fluorescence intensity measuring means for measuring an intensity in at least one wavelength range of fluorescence emitted from the specimen upon excitation by the exciting light;

an operational processing means for obtaining image data representing a fluorescence image of the specimen through an operation based on the intensity of the fluorescence;

a determining means for determining whether each of pixels forming the fluorescence image is adequate for said operation on the basis of the intensity of the fluorescence of each pixel; and said operational processing means carrying out said operation on adequate pixels to obtain values for the adequate pixels, which haven been determined to be adequate for said operation, while allotting to inadequate pixels, which have been determined not to be adequate for said operation, values which will not visually adversely affect the part of the fluorescence image corresponding to the adequate pixels;

wherein said exciting light projecting means comprises a GaN semiconductor laser as an exciting light source.

12. An apparatus for obtaining a fluorescence image comprising:

an exciting light operable to irradiate a specimen, said exciting light causing said specimen to emit fluorescence in at least one wavelength range when said exciting light is projected onto said specimen;

a fluorescent light detector which detects and measures the intensity of the emitted fluorescence to provide fluorescent measurements, said fluorescent measurements used to generate a fluorescent image of the specimen, said fluorescent image comprises a plurality of pixels;

a noise detector determining a noise value for the noise generated in the fluorescent light detector for said plurality of pixels;

a memory storing said noise value for each of said pixels;

a comparator receiving the noise value from said memory and a fluorescent measurement for a respective pixel; and a determination device receiving an output of the comparator to determine a pixel as an adequate pixel or an inadequate pixel.

13. The apparatus of claim 12 further comprising an image processor processing only the adequate pixels.

14. The apparatus of claim 12 wherein the specimen is an organic body and the fluorescence is in vivo autofluorescence.

15. The apparatus of claim 12 wherein the exciting light is a GaN semiconductor laser.

16. The apparatus of claim 12 wherein said determination device further comprises determining an adequate pixel when the noise value stored in memory for said pixel is less than the fluorescent measurement for said pixel.

17. The apparatus of claim 12 wherein the value of said inadequate pixels in the fluorescent image are assigned a value which will not visually adversely affect the part of the fluorescence image corresponding to the adequate pixels.

18. The apparatus of claim 12 wherein the noise detector individually determines a noise value for each one of said plurality of pixels.

* * * * *